US008623624B2

(12) United States Patent
Kistenmacher et al.

(10) Patent No.: US 8,623,624 B2
(45) Date of Patent: Jan. 7, 2014

(54) METHOD FOR BIOTECHNOLOGICAL PRODUCTION OF A HYDROGEN CARRIER

(75) Inventors: Hans Kistenmacher, Planegg (DE); Hans Jurgen Maass, Dresden (DE); Mathias Mostertz, Munich (DE); Karl Forchhammer, Pliening (DE)

(73) Assignee: Linde Aktiengesellschaft, Munich (DE)

( * ) Notice: Subject to any disclaimer, the term of this patent is extended or adjusted under 35 U.S.C. 154(b) by 169 days.

(21) Appl. No.: 13/051,354

(22) Filed: Mar. 18, 2011

(65) Prior Publication Data

US 2011/0256602 A1        Oct. 20, 2011

(30) Foreign Application Priority Data

Mar. 18, 2010   (DE) .......................... 10 2010 011 805

(51) Int. Cl.
 *C12N 9/00* (2006.01)
(52) U.S. Cl.
 USPC .......................... 435/189; 435/168; 435/232.1
(58) Field of Classification Search
 USPC ....................................... 435/189, 168, 232.1
 See application file for complete search history.

(56) References Cited

U.S. PATENT DOCUMENTS

2009/0104656 A1*   4/2009   Weiss et al. .................. 435/69.1

OTHER PUBLICATIONS

Z. Su et al., "Comparative Genomics Analysis of NtcA Regulons in Cyanobacteria: Regulation of Nitrogen Assimilation and its Coupling to Photosynthesis", Oxford Journals Life Sciences, Nucleic Acids Research, vol. 33, No. 16 (2005) pp. 5156-5171.
M. Nakao et al., "CyanoBase: The Cyanobacteria Genome Database Update 2010", Nucleic Acids Research, vol. 38 (2010) pp. D379-D381 http://wvvw.ncbi.nim.nih.gov/pmc/articles/PMC2808859.
J.L. Llacer et al., "Structural Basis for the Regulation of NtcA-Dependent Transcription by Proteins PipX and PII", http://www.pnas.org/content/107/35/15397.abstract (Mar. 12, 2011).
PubMed Central, Figure 1: Nucleic Acids Research, vol. 33, No. 16 (2005) pp. 5156-5171. Published Online http://ncbi.nlm.nih.gov/pmc/articles/PMC1214546/figure/fig1/.
D. Lupo et al., "The 1.3—A Resolution Structure of Nitrosomonas Europaea Rh50 and Mechanistic Implications for NH3 Transport by Rhesus Family Proteins", Proc. Natl. Acad. Sci., vol. 104, No. 49 (Dec. 4, 2007) pp. 19303-19308 http://www.ncbi/nlm.nih.gov/pubmed/18032606.
M. Garcia-Dominguez et al., "NtcA Represses Transcription of gifA and gifB, Genes That Encode Inhibitors of Glutamine Synthetase Type I from *Synechocystis* sp. PCC 6803", Mol. Microbiol., vol. 35, No. 5 (Mar. 2000) pp. 1192-1201 http://www.ncbi.nlm.nih.gov/pubmed/10712699.
KB Laichoubi et al., "The Nitrogen Interaction Network in *Synechococcus* WH5701, a Cyanobacterium with Two PipX and Two PII-like Proteins", Microbiology, vol. 157, Part 4 (Apr. 2011) pp. 1220-1228 http://www.ncbi.nlm.nih.gov/pubmed/21183574.
*Anabaena variabilis* ATCC 29413 RefSeq Genome (Accession: PRJNA58043; ID: 58043) Registration date: Oct. 21, 2010.
*Synechococcus elongatus* PCC 7942 RefSeq Genome (Accession: PRJNA58045; ID: 58045) Registration date: Oct. 21, 2010.
*Nostoc* sp. PCC 7120 RefSeq Genome (Accession: PRJNA57803; ID: 57803) Registration date: Oct. 21, 2010.
Lee et al. "The Global Nitrogen Regulator NtcA Regulates Transcription of the Signal Transducer PII (GInB) and Influences Its Phosphorylation Level in Response to Nitrogen and Carbon Supplies in the Cyanobacterium *Synechococcus* sp. Strain PCC 7942." Journal of Bacteriology May 1999, p. 2697-2702.
Lupo et al. "The 1.3-A resolution structure of Nitrosomonas europaea Rh50 and mechanistic implications for NH3 transport by Rhesus family proteins." PNAS, vol. 104, No. 49, 19303-19308; Dec. 4, 2007.
*Synechocystis* sp. PCC 6803 (Cyanobase Accession: sll1515); Retrieved from Kyoto Encyclopedia of Genes and Genomes (KEGG); Last update: Apr. 4, 2002 on Cyanobase.
*Synechocystis* sp. PCC 6803: (Cyanobase Accession: sll1911); Retrieved from Kyoto Encyclopedia of Genes and Genomes (KEGG); Last update; Dec. 28, 2001 on Cyanobase.
Garcia-Domenguez et al. "NtcA represses transcription of gifA and gifB, genes that encode inhibitors of glutamine synthetase type I from *Synechocystis* sp. PCC 6803." Molecular Microbiology (2000) 35(5), 1192-1201.
Garcia-Domenguez et al. "Glutamine synthetase inactivation by protein—protein interaction." Proc. Natl. Acad. Sci. USA vol. 96, pp. 7161-7166, Jun. 1999.
Laichoubi et al. "The nitrogen interaction network in *Synechococcus* WH5701, a cyanobacterium with two PipX and two PII-like proteins." Microbiology (2011), 157, 1220-1228.
Su et al. "Comparative genomics analysis of NtcA regulons in cyanobacteria: regulation of nitrogen assimilation and its coupling to photosynthesis." Nucleic Acids Research, 2005, vol. 33, No. 16, 5156-5171.

* cited by examiner

*Primary Examiner* — Tekchand Saidha
*Assistant Examiner* — Rama P Ramanujam
(74) *Attorney, Agent, or Firm* — Millen, White, Zelano & Branigan, P.C.

(57) ABSTRACT

The invention relates to a method for biotechnological production of a hydrogen carrier. It is proposed to culture ammonium-producing cyanobacteria in which, by increasing the nitrogenase activity and/or blocking the utilization of ammonium in the cell metabolism and/or providing an exit mechanism for ammonium via the cell membrane, the ammonium yield is increased. The ammonia generated by the cyanobacteria is made available as a hydrogen carrier.

22 Claims, No Drawings

METHOD FOR BIOTECHNOLOGICAL PRODUCTION OF A HYDROGEN CARRIER

The invention relates to a method for biotechnological production of a hydrogen carrier.

The previous supply of energy is principally based on the fossil energy carriers petroleum, coal and natural gas. However, the deposits thereof have a limited range and are becoming exhausted. Because of the limited resources of fossil energy carriers and owing to efforts for environmental and climate protection, and also for a reduced dependence on energy exporters, solutions for a more long-lasting energy provision are being worked on. Therefore, currently there is great development of the utilization of what are termed renewable energies. What are termed renewable energies are energy sources or energy carriers that are available inexhaustibly in the short term and according to human scales. Traditionally, the utilization of water power and biomass have a certain importance. Since the 1990s, in particular the utilization of wind, solar energy and biomass have greatly increased.

The energy carrier of the future is considered to be hydrogen. It can be generated, for example, by splitting water into hydrogen and oxygen using electrical power (electrolysis) that is obtained from renewable energy sources (e.g. water power, wind, solar energy, biomass). Another possibility is to generate hydrogen by thermochemical gasification of biomass.

For some time there have also been various attempts to develop methods for direct production of energy carriers using cyanobacteria or green algae. A long-followed approach is photosynthetic production of hydrogen. However, this process takes place only in traces in nature. An industrial utilization of this process has proved to be problematic, since the enzyme hydrogenase responsible for the process is very oxygen-sensitive. Therefore, organisms would first have to be constructed therefore which are tolerant to the oxygen which is formed during the photosynthesis from water, in addition to the hydrogen.

Alternative strategies which appear to have a more promising outlook are those in which the hydrogen equivalents released by solar energy are not released as free hydrogen, but are bound to carrier molecules.

It is therefore an object of the present invention to specify a method of the type in question by which a readily handleable hydrogen carrier of high energy density can be produced.

Upon further study of the specification and appended claims, other objects and advantages of the invention will become apparent.

These objects are achieved according to the invention in that ammonium formed from nitrogen or nitrogenous compounds by means of cyanobacteria via photosynthetically coupled reactions is taken off via the cell membrane of the cyanobacteria and ammonia generated therefrom is provided as hydrogen carrier.

Suitable Cyanobacterial strains for use in the invention include *Anabaena variabilis* ATCC 29413, *Nostoc* sp. strain PCC7120, and other nitrogen-fixing filamentous cyanobacteria. All cyanobacteria investigated so far encode NtcA. See the Cyanobase web-site at the world wide web portal, genome.kazusa.or.jp/cyanobase. See also Nakao et al., "CyanoBase: the cyanobacteria genome database update 2010," Nucleic Acid Res., January 2010; 38 (Database issue): D379-D381, and See also Luque, I. and Forchhammer, K. Nitrogen assimilation and C/N balance sensing. In: The Cyanobacteria: Molecular Biology, Genomics and Evolution (eds: Flores, E. and Herrero, A.). Horizon Scientific Press pp. 335-382 (2007), the disclosures of which is hereby incorporated by reference.

See also Zhengchang Su, Victor Olman, Fenglou Mao, and Ying Xu, "Comparative genomics analysis of NtcA regulons in cyanobacteria: regulation of nitrogen assimilation and its coupling to photosynthesis," Nucleic Acids Research, Vol. 33, Issue 16, pp 5156-5171 (2005), the disclosure of which is hereby incorporated by reference. This article discloses and compares the sequences for NtcA from 17 cyanobacterial strains: *Synechococcus* sp. WH 7803 (WH7803), *Prochlorococcus marinus* sp. MIT 9313 (MIT9313), *Synechococcus* sp. WH 8102 (WH8102), *Prochlorococcus marinus* sp. CCMP1375 (CCMP1375), *Prochlorococcus marinus* subsp. *pastoris* (Proch_pastoris), *Prochlorococcus marinus* sp. CCMP1986 (MED4), *Crocosphaera watsonii* WH 8501 (WH8501), *Cyanothece* sp, ATCC 51142 (*Cyanothece*), *Synechocystis* sp, PCC 6803 (PCC6803), *Nostoc* sp. PCC 7120 (PCC 7120), *Synechococcus* sp. PCC 7002 (PCC7002), *Trichodesmium* sp. IMS101 (*Trichodesmium*), *Plectonema boryanum* (*Plectonema*), *Synechococcus elongatus* PCC 6301 (PCC6301), *Synechococcus* sp. PCC 7942 (PCC7942), *Thermosynechococcus elongatus* BP-1 (*Thermosynechococcus*), and *Gloeobacter violaceus* PCC 7421 (PCC7421), With regards to genetics of cyanobacterium, see, for example, Methods for cyanobacterial genetics: Mackey, S R, Ditty J L, Clerico, E M, Golden, S S. (2007), and "Detection of rhythmic bioluminescence from luciferase reporters in cyanobacteria," in: Methods in Molecular Biology Vol 362: Chapter 8. p. 115-129, the disclosures of which is hereby incorporated by reference. See also The Cyanobacteria: Molecular Biology, Genomics and Evolution (eds: Flores, E. and Herrero, A.). Caister Academic Press (2008).

The invention uses here the following knowledge from the biology of algae and cyanobacteria:

The metabolism of green algae and cyanobacteria consists of the photosynthetic process and the Calvin cycle and also metabolic pathways attached thereto of central metabolism for synthesizing biomass. Using solar energy, the photosynthetic process, by means of the photosystem-II apparatus, cleaves water to $H^+$, $e^-$ and $O_2$. In this process, energy and reduction equivalents are obtained for cell metabolism. Cyanobacteria are able to produce ammonium from atmospheric nitrogen ($N_2$) via photosynthetically coupled reactions using the enzyme nitrogenase or from nitrate, using the enzymes nitrate reductase and nitrite reductase. Of course, the resultant ammonium is immediately assimilated to organic nitrogen compounds using enzymes, in particular the enzyme glutamine synthetase. An excess formation of ammonium is prevented by strict regulation of the participating enzymes. As soon as more ammonium is formed than can be assimilated, the ammonium-forming processes are throttled. A key role here is played by the regulation proteins PII (protein fraction II for glutamine synthetase regulation), NtcA (nitrogen control protein A) and PipX (PII-interacting protein X) which together control the activity and synthesis of the ammonia-forming enzymes. The enzyme hydrogenase, in contrast thereto, serves for energy balancing of the metabolism and for compensating for energetic surge functions and imbalances.

The consideration now underlying the invention is to take off, via the cell membrane of the cyanobacteria, the ammonium formed in the cyanobacteria via photosynthetically coupled reactions, and to utilize it in the form of ammonia as hydrogen carrier.

In order to increase the ammonium yield, preferably the ammonium-forming reactions are supported by increasing the enzymatic activity of nitrogenase.

For this purpose, preferably the following biological mechanisms are utilized:

All enzymes which participate in the synthesis of ammonium from nitrogen or nitrogenous compounds are under the control of the gene expression factor NtcA. Gene expression factors, which are frequently also termed transcription factors, are generally proteins which make possible regulated expression of a gene, Gene expression is taken to mean the biosynthesis of RNA and proteins from the genetic information. The gene expression factors can add dynamically to the DNA sections that are important for the start of transcription and are upstream of the actual gene, and thus mediate the start of transcription of the gene by the RNA polymerase. Such DNA sections are termed promoters. In this case, by means of the gene expression factors, the activity of the gene can be either suppressed or else enhanced.

For increasing the enzymatic activity of nitrogenase, then, expediently, the gene expression factor NtcA is intensely activated.

The gene expression factor NtcA is generally activated by complex formation with the co-activator PipX (PII-interacting protein X). In wild type cells, the binding of NtcA to PipX (and thereby the activation of NtcA) is controlled by the intracellular 2-oxoglutarate concentration. For intensified activation of the gene expression factor NtcA, preferably, increased formation of the co-activator PipX is stimulated. The mode of NtcA action in gene regulation in cyanobacteria is comprehensively reviewed in Luque, I. and Forchhammer, K. Nitrogen assimilation and C/N balance sensing. In: The Cyanobacteria: Molecular Biology, Genomics and Evolution (eds: Flores, E. and Herrero, A.). Horizon Scientific Press pp. 335-382 (2007), the disclosure of which is hereby incorporated by reference. See also Herrero, A., Muro-Pastor, A. M., Flores, E., Nitrogen control in cyanobacteria J. Bacterial. 183411-425 (2001).

PipX is present in every cyanobacteria) genome sequenced so far. With regards to PipX in cyanobacterium, see, e.g., Laichoubi, K. B., Beez, S, Espinosa, J., Forchhammer, K. and Contreras, A. "Nitrogen interaction network in *Synechococcus* WH5701, a cyanobacterium with two PipX and two PII-like proteins." Microbiology. 157:1221-1229 (2011), the disclosure of which is hereby incorporated by reference.

According to a preferred embodiment of the invention, a strain is produced which forms PipX to a greater extent. For this purpose, the PipX gene encoding the co-activator PipX is brought under the control of an inducible promoter which is introduced into the genome of the cyanobacterium. Particularly preferably, a promoter that is inducible by the gene expression factor NtcA is used. This achieves that, in the presence and/or addition of a sufficient amount of NtcA, the promoter of the PipX gene is activated, consequently the co-activator PipX is formed to a greater extent and by complex formation of the co-activator PipX with the gene expression factor NtcA, this is activated, which finally leads to an increase of the enzymatic activity of the nitrogenase and thus to improving the ammonium yield. development of the concept of the invention envisages that the ammonium yield is increased by blocking the utilization of the ammonium within the cyanobacterium. Thus, more ammonium is available for takeoff from the cyanobacterium. This is achieved in that the assimilation of the ammonium formed via photosynthetic reactions to produce organic nitrogen compounds in the cyanobacterium is inhibited.

An example of an inducible promotor is the NtcA-dependent gins promoter from *Synechococcus* strain PCC 7942. See, e.g., Aldehni, M. F., Sauer, J., Spielhaupter, C. Schmid, R. and Forchhammer, K., "The Signal transduction protein PII is required for NtcA-regulated gene expression during nitrogen deprivation in the cyanobacterium *Synechococcus elongatus* Strain PCC 7942," *J. Bacteriol.* 185: 2582-2591 (2003), the disclosure of which is hereby incorporated by reference.

For this purpose, preferably glutamine synthesis is genetically inhibited. This can be performed by inhibition of glutamine-forming enzymes, in particular glutamine synthetase. All cyanobacterial strain encode at least one glutamine synthetase. See, for example, Luque, I. and Forchhammer, K. Nitrogen assimilation and C/N balance sensing. In: The Cyanobacteria: Molecular Biology, Genomics and Evolution (eds: Flores, E. and Herrero, A.). Horizon Scientific Press pp. 335-382 (2007), the disclosure of which is hereby incorporated by reference.

A preferred possibility therefor is endogenous expression of inhibition proteins, in particular inhibition factors IF7 and IF17 (glutamine synthetase inhibition factors having molecular weights of 7 kDa and 17 kDa, respectively). With regards to the function of IF factors, see, for example, García-Domínguez, M., Reyes, J. C., Florencio, F. J. "Glutamine synthetase inactivation by protein-protein interaction," *Proc Nati Acad Sci USA* 96: 7161-7166 (1999), the disclosure of which is hereby incorporated by reference.

All cyanobacteria investigated so far encode glutamine synthetase inhibition factor (IF) homologues, for example, IF7: encoded by the gifA gene from *Synechocystis* PCC6803 (Cyanobase genecode: ssl1911) and IF17: encoded by the gifB gene from *Synechocystis* PCC6803 (Cyanobase genecode: sll1515). As noted above, an example of an inducible promotor is the NtcA-dependent glnB promoter from *Synechococcus* strain PCC 7942.

With regards to glutamine synthetase and IF proteins in cyanobacterium see, for example, Luque, I. and Forchhammer, K. Nitrogen assimilation and C/N balance sensing, In: The Cyanobacteria: Molecular Biology, Genomics and Evolution (eds: Flores, E. and Herrero, A.). Horizon Scientific Press pp. 335-382 (2007), the disclosure of which is hereby incorporated by reference.

Therefore, care is taken to ensure that these inhibition factors are formed in the cyanobacterium itself. This is expediently achieved in that the genes encoding the inhibition proteins are brought under control of a promoter inducible, in particular, by the gene expression factor NtcA, which promoter inducible by gene expression factor is introduced into the genome of the cyanobacterium. This means that, in the presence of and/or addition of a sufficient amount of NtcA, more inhibition proteins are formed which suppress glutamine synthetase, which blocks the internal utilization of the ammonium via glutamine synthesis.

Another advantageous possibility for genetic inhibition of glutamine synthesis is by direct influencing of the expression of the glutamine synthetase-encoding genes, in particular the glnA gene, For this purpose, expediently, the genes encoding the glutamine synthetase are brought under the control of a promoter repressed by the gene expression factor NtcA, which promoter is introduced into the genome of the cyanobacterium. This means that, in the presence and/or addition of a sufficient amount of NtcA, the formation of the enzyme glutamine synthetase is suppressed from the start, which blocks the internal utilization of ammonium via glutamine synthesis.

An example of a promoter that is repressed by NtcA is the gif promoter from *Synechocystis* PCC6803, described in García-Domínguez M, Reyes J C, Florencio F J., "NtcA represses transcription of gifA and gifB, genes that encode inhibitors of glutamine synthetase type I from *Synechocystis* sp. PCC 6803," Mol Microbiol.; 35 (5): 1192-201 (March 2000), the disclosure of which is hereby incorporated by reference.

According to a particularly advantageous embodiment of the invention, at the same time, the nitrogenase activity for ammonium formation is increased and the internal utilization of the ammonium thus formed in glutamine synthesis is blocked. In this case, preferably, NtcA-inducible promoters are used for increasing the nitrogenase activity and NtcA-repressed promoters for inhibiting glutamine synthesis. The formation of glutamine synthetase is reduced thereby to the same extent as the production of ammonium-forming genes increases. The system can be started by adding small amounts of NtcA.

A preferred development of the invention provides that an exit mechanism for the ammonium is provided via the cell membrane of the cyanobacterium. For this purpose, membrane proteins are incorporated into the cell membrane of the cyanobacterium, which membrane proteins act as bifunctional ammonium channels and make possible ammonium transport in the entry and exit directions.

Underlying this embodiment of the invention is the knowledge that the ammonium yields can be markedly increased when cells are produced which have an ammonium exit channel, The ammonium transporters present in cyanobacteria wild type cells are pure uptake transporters. If these are exchanged for bifunctional transporters, the exit of intracellular ammonium is accelerated. The bifunctional transporters used are membrane proteins which permit ammonium transport in both directions.

For this purpose, preferably genes encoding membrane proteins of organisms having known bifunctional ammonium channels are cloned into cyanobacterial expression vectors. These expression vectors are then introduced into the cyanobacteria, in such a manner that bifunctional ammonium channels are likewise formed there.

With regards to bifunctional ammonium channels, see, for example, the Rhesus-factor ammonium channels described by Lupo D, Li X D, Durand A, Tomizaki T, Cherif-Zahar B, Matassi G, Merrick M, Winkler F K., "1.3-A resolution structure of *Nitrosomonas europaea* Rh50 and mechanistic implications for NH3 transport by Rhesus family proteins," Proc Natl Acad Sci U S A. 2007 Dec. 4; 104 (49): 19303-8. Epub 2007 Nov. 21, the disclosure of which is hereby incorporated by reference. A bacterium that encodes such a Rhesus factor channel is *Nitrosomonas europaea*.

The invention provides a possibility for generating from solar energy a hydrogen carrier which has considerable advantages in comparison with free hydrogen:

Firstly, the biotechnological production of the hydrogen carrier is considerably simpler to handle than the biotechnological production of free hydrogen. A core problem in the direct production of free hydrogen by means of photosynthesis is the oxygen sensitivity of the enzyme hydrogenase that plays a considerably important part. To date, it has not been possible to express a sufficiently oxygen-resistant and fully functional hydrogenase in cyanobacteria. The invention avoids this problem in that the hydrogenase is not used for producing free hydrogen, but the ability of cyanobacteria to fix nitrogen by photosynthetically coupled reactions is exploited. The enzyme nitrogenase that participates therein supplies in a natural manner the cells with nitrogen for cell growth. In the course of evolution, refined strategies have been developed in order to protect the nitrogenase from the oxygen which is liberated in photosynthesis. Therefore, the invention makes use of a system which functions well by nature.

Secondly, the hydrogen carrier produced according to the invention is very much easier to transport and store than free hydrogen. Ammonia has a very high energy density (17.6% by weight hydrogen). It is a marketable chemical substance that can be stored under low pressure. Furthermore, the hydrogen can be released from the ammonia by metal catalysis at temperatures below 300° C.

The entire disclosure[s] of all applications, patents and publications, cited herein and of corresponding German Application No. 10 2010 011 805.2, filed Mar. 18, 2010 are incorporated by reference herein.

The preceding examples can be repeated with similar success by substituting the generically or specifically described reactants and/or operating conditions of this invention for those used in the preceding examples.

We claim:

1. A method for biotechnological production of a hydrogen carrier, comprising contacting a nitrogen or a nitrogenous compound with a transformed photosynthetic cyanobacteria which has altered expression of a plurality of genes involved in the synthesis, assimilation and transportation of the ammonium produced by said photosynthetic cyanobacteria, wherein
    (a) the products of the genes involved in the synthesis of said ammonium comprise
        (1) co-activator PII-interacting protein X (PipX) which forms a complex with a nitrogen control protein A (NtcA), wherein said PipX-NtcA complex activates said NtcA, resulting in a concomitant activation of the gene nitrogenase, which in turn increases the yield of the ammonium generated by said photosynthetic cyanobacteria; and
    (b) the products of the genes involved in the assimilation of ammonium comprise
        (1) glutamate synthatase, which assimilates ammonium into glutamate, thereby reducing the yield of ammonium; and
        (2) glutamine synthetase inhibition factors IF7 and IF17 having molecular weights of 7 kpa and 17 kpa, respectively, wherein the inhibition factors inhibit glutamine synthase, thereby inhibiting the assimilation of ammonium into glutamate and concomitantly increasing the yield of ammonium; and
    (c) the products of the genes involved in the transportation of ammonium comprise
        (1) bifunctional ammonium channels,
    wherein the expression of at least one gene in each of (a), (b) and (c) is altered in said transformed photosynthetic bacteria and wherein ammonium product is provided as said hydrogen carrier.

2. The method of claim 1, wherein the cyanobacteria comprise increased nitrogenase activity, thereby increasing the yield of ammonium generated therefrom.

3. The method of claim 2, wherein the nitrogenase activity is increased by activating a gene expression factor nitrogen control protein A (NtcA).

4. The method of claim 3, wherein the gene expression factor NtcA is activated by stimulating the increased formation of a co-activator PII-interacting protein X (PipX), and wherein formation of a complex between said NtcA and said PipX activates said NtcA.

5. The method of claim 4, wherein said increased formation of PipX is achieved by introducing into the genome of the cyanobacterium a PipX gene encoding PipX that is under the control of an inducible promoter.

6. The method of claim 5, wherein said inducible promoter is a promoter that is induced by the gene expression factor NtcA.

7. The method of claim 1, wherein one or more enzymes involved in the assimilation of the ammonium product in the cyanobacterium is inhibited.

8. The method of claim 7, wherein the assimilation of the ammonium product into glutamine is inhibited by inhibiting a glutamine-forming enzyme in said cyanobacteria.

9. The method of claim 8, wherein the enzyme that is inhibited is glutamine synthetase.

10. The method of claim 9, wherein said glutamine synthetase is inhibited by inducing the endogenous expression of one or more inhibition proteins in said cyanobacteria.

11. The method of claim 10, wherein said inhibition proteins are glutamine synthetase inhibition factors IF7 and IF17 having molecular weights of 7 kpa and 17 kpa, respectively.

12. A method of claim 11, wherein the genes encoding the inhibition proteins are brought under the control of an inducible promoter.

13. The method of claim 12, wherein said inducible promoter is a promoter inducible by the gene expression factor NtcA.

14. A method according to claim 8, wherein formation of glutamine synthetase is inhibited by directly suppressing the expression of the glutamine synthetase-encoding genes.

15. A method of claim 14, wherein formation of glutamine synthetase is inhibited by suppressing the expression of the glnA gene.

16. The method of claim 14, wherein genes encoding glutamine synthetase are brought under the control of a promoter repressed by the gene expression factor NtcA, the repressing promoter being introduced into the genome of the cyanobacterium.

17. A method according to claim 1, wherein membrane proteins are incorporated into the cell membrane of the cyanobacterium, wherein said membrane proteins act as bifunctional ammonium channels and make possible ammonium transport in the entry and exit directions.

18. The method of claim 17, wherein genes encoding membrane proteins of organisms having known bifunctional ammonium channels are cloned into cyanobacterial expression vectors and these expression vectors are introduced into the cyanobacteria.

19. The method of claim 1, wherein the cyanobacterium is *Anabaena variabilis* ATCC 29413, or *Nostoc* sp. strain PCC7120.

20. The method according to claim 6, wherein said inducible promoter is the NtcA-dependent glnB promoter from *Synechococcus* strain PCC 7942.

21. The method of claim 13, wherein said inducible promoter is the NtcA-dependent glnB promoter from *Synechococcus* strain PCC 7942.

22. The method of claim 16, wherein said promoter that is repressed by NtcA is the gif promoter from *Synechocystis* PCC6803.

* * * * *

UNITED STATES PATENT AND TRADEMARK OFFICE
CERTIFICATE OF CORRECTION

PATENT NO. : 8,623,624 B2  
APPLICATION NO. : 13/051354  
DATED : January 7, 2014  
INVENTOR(S) : Hans Kistenmacher et al.

Page 1 of 1

It is certified that error appears in the above-identified patent and that said Letters Patent is hereby corrected as shown below:

In the Claims

Column 6, line 43 reads "7 kpa and 17 kpa", should read --7 kDa and 17 kDa--;

Column 7, line 18 reads "7 kpa and 17 kpa", should read --7 kDa and 17 kDa--.

Signed and Sealed this  
Twenty-ninth Day of April, 2014

Michelle K. Lee  
*Deputy Director of the United States Patent and Trademark Office*